(12) United States Patent
Flashner-Barak et al.

(10) Patent No.: US 6,881,420 B2
(45) Date of Patent: Apr. 19, 2005

(54) COMPOSITIONS AND DOSAGE FORMS FOR GASTRIC DELIVERY OF IRINOTECAN AND METHODS OF TREATMENT THAT USE IT TO INHIBIT CANCER CELL PROLIFERATION

(75) Inventors: Moshe Flashner-Barak, Petach Tikva (IL); Vered Rosenberger, Jerusalem (IL); E. Itzhak Lerner, Petach Tikva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 5 days.

(21) Appl. No.: 10/026,573

(22) Filed: Dec. 20, 2001

(65) Prior Publication Data

US 2002/0147208 A1 Oct. 10, 2002

Related U.S. Application Data

(63) Continuation-in-part of application No. 09/887,204, filed on Jun. 22, 2001, now abandoned.
(60) Provisional application No. 60/273,428, filed on Mar. 5, 2001, and provisional application No. 60/213,832, filed on Jun. 23, 2000.

(51) Int. Cl.[7] .................................................. A61K 9/20
(52) U.S. Cl. ....................... 424/465; 424/464; 424/451; 424/452; 424/457
(58) Field of Search ................................ 424/400, 464, 424/465, 451, 452, 457

(56) References Cited

U.S. PATENT DOCUMENTS

| | | |
|---|---|---|
| 2,996,431 A | 8/1961 | Barry |
| 3,139,383 A | 6/1964 | Neville |
| 3,995,058 A | 11/1976 | Hammond et al. |
| 4,140,755 A | 2/1979 | Sheth et al. |
| 4,167,558 A | 9/1979 | Sheth et al. |
| 4,190,672 A | 2/1980 | Fahn |
| 4,434,153 A | 2/1984 | Urquhart et al. |
| 4,557,925 A | 12/1985 | Lindahl et al. |
| 4,704,285 A | 11/1987 | Alderman |
| 4,705,651 A | 11/1987 | Staibano |
| 4,721,613 A | 1/1988 | Urquhart et al. |
| 4,752,470 A | 6/1988 | Mehta |
| 4,756,911 A | 7/1988 | Drost et al. |
| 4,758,436 A | 7/1988 | Caldwell et al. |
| 4,764,380 A | 8/1988 | Urquhart et al. |
| 4,767,627 A | 8/1988 | Caldwell et al. |
| 4,853,229 A | 8/1989 | Theeuwes |
| 4,919,938 A | 4/1990 | Lovegrove et al. |
| 4,983,398 A | 1/1991 | Gaylord et al. |
| 5,007,790 A | 4/1991 | Shell |
| 5,051,262 A | 9/1991 | Panoz et al. |
| 5,198,229 A | 3/1993 | Wong et al. |
| 5,232,704 A | 8/1993 | Franz et al. |
| 5,560,933 A | 10/1996 | Soon-Shiong et al. |
| 5,599,534 A | 2/1997 | Himmelstein et al. |
| 5,674,874 A | 10/1997 | Hausheer et al. |
| 5,780,057 A | 7/1998 | Conte et al. |
| 5,837,284 A | 11/1998 | Mehta et al. |
| 5,840,756 A | 11/1998 | Cohen et al. |
| 5,958,443 A | 9/1999 | Viegas et al. |
| 6,120,803 A | 9/2000 | Wong et al. |
| 6,143,326 A | 11/2000 | Möckel et al. |
| 6,207,197 B1 | 3/2001 | Illum et al. |
| 6,261,601 B1 | 7/2001 | Talwar et al. |
| 6,271,278 B1 | 8/2001 | Park et al. |
| 6,340,475 B2 | 1/2002 | Shell et al. |
| 2002/0136744 A1 * | 9/2002 | McGlynn et al. ........... 424/400 |

FOREIGN PATENT DOCUMENTS

| | | |
|---|---|---|
| EP | 0 761 209 | 3/1997 |
| JP | H4-346919 | 12/1992 |
| WO | WO 98/11879 | 3/1998 |
| WO | WO 99/04764 | 2/1999 |
| WO | WO 99/32151 | 7/1999 |

OTHER PUBLICATIONS

US 6,034,101, 3/2000, Gupta et al. (withdrawn)

John G. Kuhn, "Pharmacology of Irinotecan," Oncology, vol. 12, No. 8, supplement No. 6, Aug. 1998, pp. 39–42.*

Hwang, Sung–Joo; Park, Haesun; Park, Kinam, "Gastric Retentive Drug–Delivery Systems", Critical Reviews in Therapeutic Drug Carrier Systems, 1998, vol. 15, Issue 3, pp. 243–284.

Chen, Jun; Park Kinam, "Synthesis and characterization of superporous hydrogel composites", Journal of Controlled Release 65, 2000, pp. 73–82.

The United States Pharmacopeia and The National Formulary, Jan. 1, 2000, 24/19, p. 2235 (1999).

Chen, Jun; Blevins, William E.; Park, Haesun; Park, Kinam, "Gastric retention properties of superporous hydrogel composites", Journal of Controlled Release 64, 2000, pp. 39–51.

Thompson et al., "Efficacy of oral irinotecan against neuroblastoma xenografts," Anti–Cancer Drugs, vol. 8, 1997, Rapid Science Publishers, pp. 313–322.

Stewart et al., "Disposition of irinotecan and SN–38 following oral and intravenous irinotecan dosing in mice," Cancer Chemother Pharmacol (1997) 40, pp. 259–265.

(Continued)

Primary Examiner—Thurman K. Page
Assistant Examiner—Rachel M. Bennett
(74) Attorney, Agent, or Firm—Kenyon & Kenyon

(57) ABSTRACT

The present invention provides oral dosage forms and compositions for administering antineoplastic agents, such as irinotecan, etoposide, paclitaxel, doxorubicin and vincristine, whose oral effectiveness is limited by pre-systemic and systemic deactivation in the GI tract. Gelling of the gastric retention vehicle composition, and in the case of solid forms concomitant expansion of the composition, retains the antineoplastic drug in the patient's stomach, minimizing pre-systemic and/or systemic deactivation of the drug.

25 Claims, No Drawings

OTHER PUBLICATIONS

Rothenberg et al., "Alternative Dosing Schedules for Irinotecan," Oncology, vol. 12, No. 8, supplement No. 6, Aug. 1998, pp. 68–71.

Drengler et al., "Phase J and Pharmacokinetic Trial of Oral Irinotecan Administered Daily for 5 Days Every 3 Weeks in Patients With Solid Tumors," Journal of Clinical Oncology, vol. 17, No. 2, Feb. 1999, pp. 685–696.

Bissery et al., "Experimental antitumor activity and pharmacokinetics of the camptothecin analog irinotecan (CPT–11) in mice," Anti–Cancer Drugs, vol. 7, 1996, Rapid Science Publishers, pp. 437–460.

John G. Kuhn, "Pharmacology of Irinotecan," Oncology, vol. 12, No. 8, supplement No. 6, Aug. 1998, pp. 39–42.

Choi et al., "Oral versus intraperitoneal administration of irinotecan in the treatment of human neuroblastoma in nude mice," Cancer Letters 124, 1998; pp. 15–21.

Zamboni et al., "Altered Irinotecan and SN–38 Disposition after Intravenous and Oral Administration of Irinotecan in Mice Bearing Human Neuroblastoma Xenografts," Clinical Cancer Reseach, vol. 4, Feb. 1998, pp. 455–462.

Beaulieu et al., "Comparative Assessment of P–Glycoprotein Expression in Mammalian Tissues by Immunoblotting," IJBC, 1999, vol. 4, pp. 253–268.

Zamboni et al., "Studies of the Efficacy and Pharmacology of Irinotecan against Human Colon Tumor Zenograft Models," Clinical Cancer Research, vol. 4, Mar. 1998, pp. 743–753.

Lowe et al. "Dependent Apoptosis Modulations the Cytotoxicity of Anticancer Agents," Cell, vol. 74, Sep. 24, 1993, pp. 957–967.

Yusuke Tanigawara, "Role of P–Glycoprotein in Drug Disposition," Therapeutic Drug Monitoring, 22: 137–140, 2000, Lippincott Williams & Williams, Inc.

Fisher et al., "MDR Expression in Normal Tissues," Hematology/Onocology Clinics of North America, Drug Resistance in Clinical Oncology and Hematology, vol. 9, No. 2, Apr. 1995, pp. 319–337.

Hung Liang Tai, "Technology evalution: Valspodar, Novartis AG," Current–Opinion in Molecular Therapeutics, 2000; 2/4 (459–467).

M.F. Fromm, "P–glycoprotein: a defense mechanism limiting oral bioavailability and CNS accumulation of drugs," International Journal of Clinical Pharmacology and Therapeutics, vol. 38, No. 2/2000 (69–74).

DeMario et al., "Oral Chemotherapy: Rationale and Future Directions," Journal of Clinical Oncology, vol. 16, No. 7 (Jul.), 1998: pp. 2557–2567.

Sparreboom et al., "Limited oral bioavailability and active epithelial excretion of paclitaxel (Taxol) caused by P–glycoprotein in the intestine," Proc. Natl. Acad. Sci. USA, vol. 94, pp. 2031–2035, Mar. 1997 Pharacology, pp. 2031–2035.

Takehiko Kunimoto et al., "Antitumor Activity of 7–Ethyl–10–[4–(1–piperidino)–1–piperidino]carbonyloxy–camptothecin, a Novel Water–soluble Derivative of Camptothecin, Against Murine Tumors," Cancer Research, vol. 47, No. 22, Nov. 15, 1987, pp. 5944–5947.

* cited by examiner

COMPOSITIONS AND DOSAGE FORMS FOR GASTRIC DELIVERY OF IRINOTECAN AND METHODS OF TREATMENT THAT USE IT TO INHIBIT CANCER CELL PROLIFERATION

CROSS-REFERENCE TO RELATED APPLICATIONS

This application claims the benefit of provisional application Ser. No. 60/273,428, filed Mar. 5, 2001 and is a continuation-in-part of U.S. patent application Ser. No. 09/887,204, filed Jun. 22, 2001 now abandoned, which in turn claims priority of provisional application Ser. No. 60/213,832, filed Jun. 23, 2000, all of which are incorporated herein by reference.

FIELD OF THE INVENTION

The present invention relates to antineoplastic agents and in particular to antineoplastic agents whose oral effectiveness is limited by pre-systemic and systemic deactivation. The present invention further relates to orally administered gastric delivery systems for releasing antineoplastic agents in the stomach of a patient.

BACKGROUND OF THE INVENTION

In cancer chemotherapy it is necessary to eradicate all tumor cells or the surviving cells will continue to replicate unchecked and the cancer will return. Toxic side effects of antineoplastic drugs impose a ceiling upon the intensity of dosing per treatment cycle. Each cycle in a program of treatment kills less than 99% of tumor cells and some regrowth of cancer cells occurs between cycles. The proportion of tumor cells killed in a treatment cycle typically remains constant throughout the program even when the disease responds well to the chemotherapy. It is therefore indicated in cancer chemotherapy to use the highest dose of an antineoplastic agent that a patient is able to tolerate and to administer the drug as frequently as possible. *Goodman & Gilman's The Pharmacological Basis of Therapeutics* 1230 (9th ed. 1996).

Many antineoplastic agents used in cancer chemotherapy are administered directly to the patient's bloodstream in order to bypass problems of absorption and pre-systemic metabolism. Intravenous delivery is not amenable to self administration in a home setting and usually necessitates hospitalization at least as an outpatient. Intraveneous dosing schedules, although of high intensity, are typically less frequent than they would be if the drug could be administered in a home setting by means other than intravenous injection. Chemotherapy with many antineoplastic agents could benefit from a higher frequency dosing schedule for better efficacy, in some cases in conjunction with lower dosing in order to reduce adverse effects.

Irinotecan (CPT-11) is an example of a drug that is currently administered by i.v. for which extended duration of therapy is more efficacious than higher dose intermittent therapy. Thompson, J. et. al. "Efficacy of oral irinotecan against neuroblastoma xenografts" *Anti-Cancer Drugs* (1997), 8, 313–332; Drengler, R. L. et. al., "Phase I and Pharmacokinetic Trial of Oral Irinotecan Administered Daily for 5 Days Every 3 Weeks in Patients with Solid Tumors", *Journal of Clinical Oncology* (1999), 17, 685–696; Zamboni, W. C. et. al. "Studies of the Efficacy and Pharmacology of Irinotecan Against Human Colon Tumor Xenograft Models" *Clin. Cancer Res.* (1998), 4, 743–753.

Irinotecan is a water-soluble camptothecin derivative that interrupts DNA replication by binding to the topoisomerase I enzyme responsible for cutting and religating single DNA strands. Irinotecan is most effective against a particular tumor cell during the DNA synthesis phase of cell replication, making it a phase sensitive drug. Only a fraction of tumor cells are vulnerable to cell death during a treatment cycle with irinotecan because only a fraction will be caught in the susceptible phases of replication.

It has been shown in an animal model that lower dose daily administration of irinotecan is as effective and less toxic than less frequent higher dose administration. Houghton, P. J. et. al. "Efficacy of Topoisomerase I Inhibitors Topotecan and Irinotecan Administered at Low Dose Levels in Protracted Schedules to Mice Bearing Xenografts of Human Tumors" *Cancer Chemother. Pharmacol.* (1995), 36, 393–403; Thompson, J. et. al. "Efficacy of Systemic Administration of Irinotecan Against Neuroblastoma Xenografts" *Clin. Cancer Res.* (1997), 3, 423–432.

The greater efficacy of extended duration therapy and the reduced toxicity of lower dose daily administration make irinotecan an excellent candidate for oral delivery as a convenient way of achieving lower dose protracted schedules. Rothenberg, M. L. et. al. "Alternative Dosing Schedules for Irinotecan", *Oncology* (1998), 8 suppl 6, 68–71.

Oral delivery, with the convenience of self administration and home dosing, would ease the burden on the patient and care giver imposed by a more frequent dosing schedule. However, the oral bioavailability of irinotecan is reported to be only about 20% of its iv. bioavailability. Kuhn, J. G., "Pharmacology of Irinotecan" *Oncology*(1998), 12 supp. 6, 39–42; Drengler, R. L., Ibid. Serious problems of absorption and pre-systemic metabolism of irinotecan need to be overcome before oral delivery becomes available as a treatment option.

Irinotecan is a metabolic precursor of 7-ethyl-10-hydroxycamptothecin. The metabolite is also known by the designation SN-38. SN-38 has been found to be approximately a thousand times more potent an inhibitor of topoisomerase I than irinotecan. SN-38 is formed by hydrolysis of the ester side chain of irinotecan by carboxylesterases in the body. Steward, C. F. et. al., "Disposition of Irinotecan and Sn-38 Following Oral and Intravenous Irinotecan Dosing in Mice" *Cancer Chemother. Pharmacol.* (1997), 40, 259–265; Kuhn, J. G., "Pharmacology of Irinotecan" *Oncology* (1998), 12 supp. 6, 39–42. While the main site of metabolism of irinotecan to the more active SN-38 is the liver, there is considerable activity of carboxylesterase in the upper GI tract. Kuhn, J. G. Ibid; Takamura, K. et. al., "Involvement of Beta-glucuronidase in Intestinal Microflora in the Intestinal Toxicity of the Anti Tumor Camptothecin Derivative Irinotecan Hydrochloride (CPT-11) in Rats" *Cancer Res.* (1996), 56, 3752–3757.

Both irinotecan and SN-38 can exist in a closed ring lactone form and an open, hydroxy acid form. Only the lactone form of either compound is active against tumors. Steward, C. F. et. al. Ibid; Drengler, R. L. et. al. Ibid. Acidic conditions favor the lactone form of the drug. Basic conditions favor the hydroxy acid form.

If irinotecan can be released in the stomach, the low gastric pH will keep more of the irinotecan in the active lactone form. Therefore, more of the SN-38 that is produced by carboxylesterases in the gut should be in the active lactone form. Steward, C. F. et. al. Ibid; Drengler, R. L. et. al. Ibid. This assumption of a higher ratio of active SN-38 to inactive SN-38 by oral delivery has been borne out in animal models and in a human phase I study. Zamboni, W. C. et. al. Ibid; Kuhn J. G. Ibid; Drengler, R. L. et. al. Ibid. Delivery and absorption of the irinotecan preferentially in the stomach should improve its oral systemic bioavailability against tumor cells by increasing the proportion of SN-38 that reaches the tumor in active form.

Other cell cycle specific drugs are likely to benefit from more frequent dosing which extends the duration of drug presentation to the tumor and catches more of the cells in the sensitive phase of their cycle. The benefit can be realized whether they be of the topoisomerase mechanism or other phase sensitive mechanism (e.g. paclitaxel which works by stabilizing microtubule polymerization). Etoposide and paclitaxel are two other phase sensitive antineoplastic agents that could be used more efficaciously with frequent lower oral dosing as opposed to intermittent higher dosing by i.v. Etoposide binds to topoisomerase II and DNA resulting in double stranded DNA breaks that a cell cannot repair. Etoposide undergoes highly variable absorption when administered orally and exhibits on average about 50% of its i.v. potency. *Goodman & Gilman's The Pharmacological Basis of Therapeutics* 1262 (9th ed. 1996). Paclitaxel is not currently administered orally.

One of the factors that causes the low oral bioavailability of etoposide and paclitaxel is removal by the P-glycoprotein ("Pgp") efflux pump mechanism of cells at the site of intestinal absorption. Lo, Y. L.; Huang, J. D., "Comparison of Effect of Natural or Artificial Rodent Diet on Etoposide Absorption in Rats" *In Vivo* (1999), 13, 51–55; Britten, C. D. et. al., "Oral Paclitaxel and Concurrent Cyclosporin A: Targeting Clinically Relevant Systemic Exposure to Paclitaxel" *Clin. Cancer Res.* (2000), 6, 3459–3468; Fromm, M. F., "P-glycoprotein: a Defense Mechanism Limiting Oral Bioavailability and CNS Accumulation of Drugs" *Int. J. Clin. Pharmacol. Ther.* (2000), 38, 69–74; Terwogt, J. M. M., et. al. "Co-administration of Oral Cyclosporin a Enables Oral Therapy with Paclitaxel" *Clin Cancer Res* (1999), 5, 3379–3384; Sparreboom, A. et. al. "Limited Oral Bioavailability and Active Epithelial Excretion of Paclitaxel (Taxol) Caused by P-glycoprotein in the Intestine" *PNAS* (1997), 94, 2031–2035.

Pgp efflux pump activity is also relevant to other antineoplastic agents such as doxorubicin and vincristine and to anti-HIV drugs. Lum, B. L.; Gosland, M. P., "MDR Expression in Normal Tissues: Pharmacologic Implications for the Clinical Use of P-glycoprotein Inhibitors" *Hematol Oncol. Clin. North Am.* (1995), 9, 319–336; Aungst, B. J., "P-glycoprotein, Secretory Transport, and Other Barriers to the Oral Delivery of Anti-hiv Drugs" *Adv. Drug Deliv. Rev.* (1999), 39, 105–116.

Research is underway to develop new agents that are not susceptible to p-glycoprotein efflux and to develop agents that inhibit the Pgp efflux pump. Morseman, J. M.; McLeod, H. L., "Taxane Chemotherapy and New Microtubule-Interactive Agents" *Curr. Opin. Oncol. Endro. Metab. Invest. Drugs* (2000), 2, 305–311; Polizzi, D. et. al., "Oral Efficacy and Bioavailability of a Novel Taxane" *Clin. Cancer Res.* (2000), 6, 2070–2074; Nicoletti, M. I. et. al. "IDN5109, a Taxane with Oral Bioavailability and Potent Antitumor Activity" *Cancer Res.* (2000), 60, 842–846; Sikic, B. I., Ibid; Mistry, P., Ibid; Millward, M. J.; Lieu, E. A.; Robinson, A.; Cantwell, B. M. J., "High Dose Tamoxifen with Etoposide: a Study of a Potential Multi-drug Resistance Modulator" *Oncology-Switzerland* (1994), 51, 79–83; Raderer, M.; Scheithauer W., "Clinical Trials of Agents That Reverse Multi-drug Resistance: a Literature Review" *Cancer* (1993), 72, 3553–3563; Britten, C. D., Ibid; Tai, H. L., "Technology evaluation: Valspodar, Novartis AG" *Curr. Opin. Mol. Ther.* (2000), 2, 459–467; Terwogt, J. M. M., Ibid.

However, new agents are not a timely solution to the problem of pre-systemic deactivation and Pgp efflux pump removal. Development and testing of new agents, whether anti-cancer agents that are unaffected by the efflux pump or blockers of the efflux pump, will take many years with unpredictable results in terms of efficacy and adverse events. The use of known potent efflux pump blocking agents like cyclosporin, tamoxifen, verapamil in cancer chemotherapy exposes the body to the known potent effects of these drugs as well as their adverse event profiles, all as side effects of the efflux pump blocking.

If drug delivery could be used with the known effective antineoplastic agents to minimize the effects of the Pgp pump, improved oral administration could be realized without the disadvantages described above and without high concomitant doses of Pgp efflux pump blocker drugs.

Some cells that are resistant to etoposide demonstrate amplification of the MDR-1 gene that encodes the Pgp drug efflux transporter. Lowe et. al. *Cell*, 1993, 74, 957–967. The Pgp efflux pump also has been found in tumor cells. Sikic, B. I., "Modulation of Multidrug Resistance: a Paradigm for Translational Clinical Research" *Oncology* (1999) 13 A, 183–189; Mistry, P. et. al. "In Vivo Efficacy of Xr9051, a Potent Modulator of P-glycoprotein Mediated Multidrug Resistance" *Br. J. Cancer* (1999) 79, 1672–1678; Naito, M.;Tsuro, T., "Therapeutic Approach to Drug Resistant Tumors" *Ther Drug Monit* (1998), 20, 577–580.

However, Pgp expression was consistently found to be low in the stomach cells of five mammalian species. Beaulieu, E; Demeule, M.; Jette, L.; Beliveau, R., "Comparative Assessment of P-glycoprotein Expression in Mammalian Tissues by Immunoblotting" *Int. J. Bio Chromatog* (1999), 4, 253–269. Oral administration and absorption of etoposide, paclitaxel, doxorubicin and vincristine preferentially in the stomach should improve their systemic bioavailability.

Cancer chemotherapy with antineoplastic agents whose oral effectiveness is limited by pre-systemic and systemic deactivation or removal would greatly benefit if the antineoplastic agent could be administered orally and then released in the patient's stomach so that it would be absorbed predominantly from the patient's stomach, jejunum or duodenum.

Pharmaceutical formulation specialists have developed techniques for retaining drugs in a patient's stomach over time. One of the general techniques is intragastric expansion, wherein expansion of the dosage form prevents it from passing through the pylorus. The diameter of the pylorus varies between individuals from about 1 to about 4 cm, averaging about 2 cm. An expanding gastric retention dosage form must expand to at least 2 cm×2 cm in two dimensions to cause gastric retention, though a size of 2.5 cm×2 cm is more desirable.

One type of intragastric expanding dosage form uses hydrogels to expand the dosage form upon contact with gastric fluid to sufficient size to prevent its passage through the pylorus. An example of such a dosage form is described in U.S. Pat. No. 4,434,153. The '153 patent discloses a device for executing a therapeutic program after oral ingestion, the device having a matrix formed of a non-hydrated hydrogel and a plurality of tiny pills containing a drug dispersed throughout the matrix.

One of the major problems with intragastric expanding hydrogels is that it can take several hours for the hydrogel to become fully hydrated and to expand to sufficient size to cause it to be retained in the stomach. Hwang, S. et al. "Gastric Retentive Drug-Delivery Systems," *Critical Reviews in Therapeutic Drug Carrier Systems*, 1998, 15, 243–284 Since non-expanding dosage forms remain in the stomach on average for about 1 to 3 hours, there is a high probability that known expanding dosage forms like that of the '153 patent will pass through the pylorus before attaining a sufficient size to obstruct passage. The rate-limiting factor in the expansion of ordinary hydrogels is the rate of diffusion of water to non-surfacial hydrogel material in the dosage form. Conventional hydrogels are not very porous when they are dry, so transport of water into the hydrogel can be slow. In addition, a low permeability gelatinous layer forms on the surface of wetted hydrogel, which further slows transport of water into the hydrogel.

One approach to solving the problem of slow expansion has been the development of superporous hydrogels. Superporous hydrogels have networks of pores of 100 $\mu$m diameter or more. At that diameter, the pores are able to rapidly transport water deep into the superporous hydrogel by capillary action. Water reaches the non-surfacial hydrogel material quickly resulting in a rapid expansion of the superporous hydrogel to its full extent. Superporous hydrogels are still under development and have not been approved for pharmaceutical use by the U.S. Food and Drug Administration. There are also shortcomings attendant to the use of superporous hydrogels. They tend to be structurally weak and some are unable to withstand the mechanical stresses of the natural contractions that propel food out of the stomach and into the intestine. The superporous hydrogels tend to break up quickly into particles too small to be retained.

Chen, J. and Park, K. *Journal of Controlled Release* 2000, 65, 73–82, describes a superporous hydrogel whose mechanical strength is improved by the polymerization of precursor hydrogel monomers in the presence of several superdisintegrants. The result of the polymerization described by Chen and Park is a substance having interconnecting cross-linking networks of polyacrylate and, e.g., cross-linked carboxymethyl cellulose sodium. Such interconnecting networks are not expected to have the same physical properties as conventional hydrogels made from the same precursor hydrogel monomers.

Another general strategy for retaining dosage forms in the stomach is intragastric floatation, as exemplified in U.S. Pat. Nos. 4,140,755 and 4,167,558. Intragastric floatation systems are less dense than gastric fluid and avoid passage through the pylorus by floating on top of the gastric fluid. These systems generally take one of three forms. Hydrodynamically balanced floating systems comprise capsules of the active ingredient and a hydrogel that forms a gelatinous coating upon contact with water that slows further uptake of water. In one example of such a system, a capsule containing the non-hydrated hydrogel and an active ingredient dissolves upon contact with gastric fluid. The hydrogel then comes into contact with gastric fluid and forms a gelatinous coating on the surface. The gelatinous coating traps air inside the hydrogel thereby making the mass buoyant. Expansion of the hydrogel also makes it less dense and therefore more buoyant. Another form of intragastric floatation system is a gas generating system, which evolves gas upon contact with water. Gas bubbles trapped in the dosage form make it buoyant. Another variation on the intragastric floatation systems are low density core systems, wherein the active ingredient is coated over a low density material like puffed rice.

The floating dosage forms and expanding dosage forms previously described operate by different gastric retention mechanisms, each with its own requirements to be effective. A floatation system must remain buoyant even while absorbing gastric fluid. An expanding system must expand rapidly to a size sufficient to obstruct transit into the intestine and yet be small enough in its non-hydrated state to be swallowed.

The present invention includes dosage forms for gastric delivery of antineoplastic agents in embodiments wherein the dosage form expands as well as in embodiments wherein the dosage form expands and generates gas for floatation.

SUMMARY OF THE INVENTION

Delivery to and absorption through parts of the gastrointestinal (GI) tract that have less activity for detrimental pre-systemic metabolism or less activity of the Pgp efflux pump will enhance the oral bioavailability of antineoplastic agents that are (1) amenable to absorption through the stomach, jejunum or duodenum and (2) which have poor oral bioavailability attributable either to the Pgp efflux pump or to pre-systemic deactivation.

Irinotecan has increased oral bioavailability if delivered to the stomach, without increased side effects. Gastric release of irinotecan delivers it to the acidic environment of the stomach which is advantageous for minimizing ring-opening of the lactone form of the drug to the inactive hydroxyacid form. A greater proportion irinotecan is thus presented to the carboxylesterase enzymes in the GI tract in active form. A greater amount of SN-38 is produced in active form which enhances the overall in vivo potency of irinotecan.

In its particulars, the present invention provides a solid pharmaceutical dosage form comprising, as an active ingredient, an antineoplastic agent that is capable of absorption through the lining of the stomach, jejunum or duodenum of a human patient and a gastric retention vehicle composition comprising a hydrogel, wherein the dosage form expands by a factor of three or more, more preferably five or more, upon contact with gastric fluid or simulated gastric fluid and wherein after ingestion by a human patient the gastric retention vehicle composition expands to retain the dosage form in the stomach for a prolonged period of time, preferably three hours or more. The solid dosage form may be in the form of a tablet or capsule containing the antineoplastic agent and the gastric retention vehicle composition.

The invention further provides liquid compositions comprising, as an active ingredient, an antineoplastic agent that is capable of absorption through the lining of the stomach, jejunum or duodenum of a human patient and a gastric retention vehicle composition comprising a gelling agent wherein after ingestion by a human patient the gastric retention vehicle composition precipitates or gels in the patient's stomach to retain the pharmaceutical composition in the patient's stomach for a prolonged period of time, preferably three hours or more, wherein the antineoplastic agent is released from the precipitated or gelled pharmaceutical composition into the patient's stomach over a prolonged period of time.

The invention also provides methods of inhibiting cell proliferation in a tumor with the dosage forms and liquid pharmaceutical compositions of the invention. The invention further provides unit dosages of antineoplastic agents for treatment of neoplastic diseases with the novel dosage forms of the invention. Such neoplastic diseases include such widespread life-threatening diseases as breast, testicular and lung cancer. Methods of treating these diseases by repeated oral administration of the unit dosages are also provided.

DETAILED DESCRIPTION OF THE INVENTION

The present invention provides solid dosage forms and liquid compositions for enhanced systemic delivery of antineoplastic agents. "Systemic delivery" means delivery of the antineoplastic agent through the bloodstream to a tumor in the patient's body. "Enhanced systemic delivery" means an increase in the amount of antineoplastic agent that reaches the tumor through the bloodstream relative to the amount delivered by a conventional orally administered non-gastric retention dosage form or liquid composition containing the same amount of the antineoplastic agent. Enhancement in systemic delivery generally correlates with increased availability of the agent and/or an active metabolite thereof in the patient's blood (bioavailability).

The term "gastric fluid" means the endogenous fluid medium of the stomach, including water and secretions, or simulated gastric fluid. "Simulated gastric fluid" means any fluid that is generally recognized as providing a useful substitute for authentic gastric fluid in experiments designed to assess the chemical or biochemical behavior of substances in the stomach. One such simulated gastric fluid is USP Gastric Fluid TS, without enzymes. *United States Pharmacopeia and National Formulary* 24/19 p. 2235 (1999). Thus, it will be understood that throughout this disclosure and in the claims "gastric fluid" means authentic gastric fluid or simulated gastric fluid.

The dosage forms and compositions of the present invention are adapted to release the antineoplastic agent according to any of a wide variety of immediate and controlled release profiles. As used herein "immediate release" means that release of the antineoplastic agent is not significantly delayed by means of a protective coating or embedding in a matrix. The excipients used to achieve immediate release typically dissolve or disperse rapidly in gastric fluid. "Sustained release" means release of the antineoplastic agent from the dosage form over a longer period of time than the immediate release time of the same antineoplastic agent from an equivalent dosage in an immediate release formulation. "Delayed release" means that there is a period of time after the dosage form contacts gastric fluid during which the antineoplastic agent either is not released or is released at a rate that is not therapeutically effective for the purpose that the drug has been administered to the patient. "Burst release" means release of most of the antineoplastic agent over a short period of time, typically less than 30 minutes. "Pulsed release" means release of the antineoplastic agent over two or more time periods separated by a period of time in which either the antineoplastic agent is not release or is released at a rate that is not therapeutically effective for the purpose that the drug has been administered to the patient. Burst release, pulsed release and sustained release may be coupled with delayed release so that release of the antineoplastic agent according to that profile begins after a delay period in which the antineoplastic agent either is not released or is released at a rate that is not therapeutically effective for the purpose that the drug has been administered to the patient. The term "controlled release" is used inclusively to mean delayed release; sustained release, including delayed sustained release; burst release, including delayed burst release; pulsed release, including delayed pulsed release; and any release other than immediate release.

The solid dosage forms and liquid compositions of the present invention contain a gastric retention vehicle composition (alternatively "gastric retention delivery system" or "GRDS") and an antineoplastic agent that is capable of being absorbed through the lining of the stomach, jejunum or duodenum of a cancer patient. The solid dosage forms of the invention as described in their particulars below are adapted for administration to human patients. Adjustments in dosage form size and dosage so as to adapt a solid dosage form of the invention for other mammals, which are also patients as the term is used in this disclosure, is within the skill level of those in the art.

Solid dosage forms and liquid compositions according to the present invention are administered to the patient orally. The antineoplastic agent is released from the dosage form in the patient's stomach. The antineoplastic agent is then absorbed through the lining of the stomach, jejunum or duodenum and passes into the patient's bloodstream. Systemic delivery of the antineoplastic agent to the tumor is increased by the solid dosage forms and liquid compositions of this invention by releasing the antineoplastic agent in the stomach, which avoids pre-systemic deactivation or degradation of the agent in the patient's lower GI tract (i.e. ileum and colon).

As used herein an "antineoplastic agent" is an agent that inhibits cell proliferation in a tumor and prodrugs, solvates, molecular complexes and pharmaceutically acceptable salts and derivatives of the agent. Antineoplastic agents that may be administered to a patient using the solid dosage forms and liquid compositions of this invention include any antineoplastic agent that is delivered to a tumor by means of the patient's bloodstream and which is adversely affected by the p-glycoprotein efflux pump in the small intestine or by the pH of the small intestine. Such antineoplastic agents include irinotecan, etoposide, paclitaxel, doxorubicin and vincristine, especially irinotecan, etoposide and paclitaxel. In a particularly preferred embodiment, the antineoplastic agent is irinotecan. One reason that irinotecan is especially preferred is that the ability of the solid dosage forms and liquid compositions of the invention to release irinotecan in the stomach over an extended period provides a unique benefit with irinotecan since a greater proportion of irinotecan is converted into the highly active metabolite SN-38 before entering the high pH environment of the small intestine. This results in production of more active-form SN-38.

The gastric retention vehicle compositions of this invention form a gelatinous mass upon contact with gastric fluid. The gastric retention vehicle compositions may be in either a solid form or a liquid form.

Preferred solid gastric retention vehicle compositions for solid dosage forms contain a hydrogel and, optionally, a superdintegrant and/or tannic. Similar compositions, wherein a superdisintegrant and tannic acid are incorporated, are described in commonly-assigned, co-pending U.S. patent application Ser. No. 09/887,204, which is hereby incorporated by reference in its entirety.

A hydrogel is a polymeric material that can absorb more than 20% of its weight in water while maintaining a distinct three-dimensional structure. In their hydrated condition they swell to an equilibrium volume, are elastically deformable but virtually immune to plastic deformation. In their non-hydrated state, hydrogels may be structurally rigid. As used herein, "hydrogels" include dry polymers that swell in aqueous environments in addition to the water-swollen polymers. The preferred hydrogel of the gastric retention vehicle composition is hydroxypropyl methylcellulose (HPMC), either alone or in combination with hydroxypropyl cellulose (HPC) and/or a cross-linked acrylate polymer. Preferably, the HPMC has a molecular weight of from about 4000 to about 100,000 a.u. and a viscosity grade of about 8000 mPa·s or less. HPMC is commercially available under the trade name Methocel® from Dow Chemical Co.

Hydroxypropyl cellulose suitable for use in the gastric retention vehicle composition preferably has a molecular weight in the range of from about 80,000 to about 1.2 million, more preferably from about 1.0 million to about 1.2 million. HPC is commercially available under the trade name Klucel® from Hercules Inc.

Suitable cross-linked acrylate polymers include polyacrylic acid crosslinked with allyl sucrose commercially available under the trade name Carbopol® (BF Goodrich Chemical Ltd.) and polyacrylic acid cross linked with divinyl glycol.

The most preferred hydrogel of the present invention is a mixture of HPMC and HPC in a weight ratio of from about 1:3 to about 5:3.

Other polymeric substances that absorb water may be substituted for the preferred hydrogels of the invention. According to the teachings of U.S. Pat. No. 5,972,389 polyethylene oxide may be used as a swellable polymer, while U.S. Pat. No. 4,434,153 discloses a wide variety of other water swellable polymers that also may provide acceptable substitutes for the HPMC and HPMC/HPC mixtures that have been found best-adapted for practice of the invention. U.S. Pat. Nos. 5,972,389 and 4,434,153 are hereby incorporated by reference in their entirety.

The solid form gastric retention vehicle composition may further include tannic acid. Tannic acid, also called tannin, gallotannin and gallotannic acid, is a naturally occurring constituent of the bark and fruit of many trees. The term "tannins" conventionally refers to two groups of compounds, "condensed tannins" and "hydrolyzable tannins." *Merck Index* monograph No. 8828 (9th ed. 1976). The hydrolyzable tannins are sugars that are esterified with one or more (polyhydroxylarene) formic acids. One common polyhydroxylarene formic acid substituent of tannic acid is galloyl (i.e. 3,4,5-trihydroxybenzoyl). Another common polyhydroxylarene formic acid substituent of tannic acid is meta-digallic acid. A common sugar moiety of tannic acid is glucose. Preferably, USP grade tannic acid is used.

The gastric retention vehicle composition optionally also includes a superdistintegrant. Superdisintegrants are disintegrants that expand upon contact with water. Preferred superdisintegrants of the present invention expand to at least double their non-hydrated volume on contact with water. Exemplary of these superdisintegrants are cross-linked carboxymethyl cellulose sodium (a.k.a. croscarmellose sodium), sodium starch glycolate and cross-linked polyvinyl pyrollidone (a.k.a. crospovidone). Croscarmellose sodium is commercially available from FMC Corp. under the tradename Ac-Di-Sol® and from Avebe Corp. under the tradename Primellose®. Sodium starch glycolate is commercially available from Penwest Pharmaceuticals Co. under the tradename Explotab® and from Avebe Corp. under the tradename Primojel®. Crospovidone is commercially available from BASF Corp. under the tradename Kollidon®. CL and from International Specialty Chemicals Corp. under the tradename Polyplasdone®. The most preferred superdisintegrant is sodium starch glycolate.

More preferred gastric retention vehicle compositions for use in solid dosage forms of the invention contain HPMC, optionally HPC, tannic acid, and a superdisintegrant selected from the group consisting of crosspovidone, croscarmellose sodium and sodium starch glycolate and mixtures thereof.

An especially preferred solid form gastric retention vehicle composition (particularly for tableting) comprises, in a weight ratio exclusive of any other excipients that may be present, from about 20 wt. % to about 70 wt. % hydrogel (e.g. HPMC or HPMC+HPC), from about 25 wt. % to about 75 wt. % superdisintegrant and from about 2 wt. % to about 10 wt. % tannic acid. Within these ranges, a yet more preferred gastric retention vehicle composition for tableting comprises from about 30 wt. % to about 55 wt. % superdisintegrant, about 5 wt. % (±2 wt. %) tannic acid, plus an amount of hydrogel sufficient to bring the total to 100%.

When a mixture of HPMC and HPC is selected as the hydrogel and sodium starch glycolate is selected as the superdisintegrant, the gastric retention vehicle composition preferably comprises from about 10 wt. % to about 20 wt. % HPMC, from about 45 wt. % to about 50 wt. % HPC, about 25 wt. % to about 35 wt. % sodium starch glycolate and about 4 wt. % to about 10 wt. % tannic acid.

An alternative preferred gastric retention vehicle composition containing HPMC, HPC further comprises croscarmellose sodium. The formulation may comprise from about 10 wt. % to about 30 wt. % HPMC, from about 40 wt. % to about 60 wt. % HPC, about 7 wt. % to about 35 wt. % croscarmellose sodium and about 4 wt. % to about 10 wt. % tannic acid.

Having specifically described novel gastric retention vehicle compositions that are best known compositions for use with antineoplastic agents, it is to be understood that gastric retention of antineoplastic agents also may be achieved using other known gastric retention vehicle compositions, such as hydrogel matrix compositions as described in U.S. Pat. No. 4,642,233, or multicomponent systems like that of U.S. Pat. No. 5,780,057. U.S. Pat. Nos. 4,642,233 and 5,780,057 are hereby incorporated by reference in their entirety.

Solid gastric retention dosage forms of the invention may be expanding tablets or capsules.

Expanding tablets may be prepared by compacting the gastric retention vehicle composition, antineoplastic agent and, optionally, other excipients, as a powder blend or granulate in any type of tableting equipment known to the pharmaceutical arts.

Expanding tablets may contain the antineoplastic agent dispersed in the gastric retention vehicle composition. The antineoplastic agent may be dispersed as a powder or crystals in the gastric retention vehicle composition or may be incorporated into beads, pills (U.S. Pat. No. 4,642,233), pellets, microcapsules, microspheres, microgranules, nanocapsules or nanospheres and the like that are embedded within the gastric retention vehicle composition.

Expanding tablets may be prepared conventionally by dry blending, dry granulation or wet granulation, followed by compaction of the resulting tableting composition in a tableting machine. Granulation techniques will now be illustrated with an illustrative gastric retention vehicle composition that includes a superdisintegrant and tannic acid.

In dry granulation, the gastric retention vehicle composition is blended dry and then compacted into a slug or a sheet and then comminuted into compacted granules. It will be appreciated that the processes of slugging or roller compaction, followed by comminution and recompression render the hydrogel, superdisintegrant and tannic acid intragranular in the final dosage form. The antineoplastic agent may also be provided intragranularly by blending it with the gastric retention vehicle composition prior to compaction and comminution. Alternatively, the antineoplastic agent, hydrogel, superdisintegrant or tannic acid may be added after comminution, which results in that (or those)

ingredient(s) being extragranular. The resulting tableting composition or granulate may be used to prepare an expanding tablet or capsule by any of the methods described below or any other means.

In wet granulation, the gastric retention vehicle composition and antineoplastic agent may be granulated using a water:alcohol mixture or an alcohol as a granulation solvent by standard granulation techniques known in the art. The granulate may then be dried and optionally milled and sieved. The hydrogel, superdisintegrant, tannic acid or antineoplastic agent may be added to one or more of the wet granulated ingredients either before or after compaction, in which case an ingredient added after granulation would be extragranular in the final dosage form. After drying, the tabletting composition, or granulate, prepared by wet granulation may be used to prepare an expanding tablet or capsule by any of the methods described below or any other means.

In dry blending, the hydrogel, superdisintegrant, tannic acid, antineoplastic agent and any other desired excipients are blended in powder form prior to direct compression tableting.

The tableting composition prepared by dry granulation, wet granulation or dry blending may be compacted following conventional compression and direct compression techniques. In direct compression, the tableting composition has been dry blended. Direct compression produces a more uniform tablet without granules. Excipients that may be added to the tableting composition which are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in the particular formulation challenges of direct compression tableting.

In some dosage forms, controlled release of the antineoplastic agent may be provided by applying a coating to the antineoplastic agent. Thus, where the foregoing description of making tablets has described mixing, blending, granulating, compressing, etc. of the antineoplastic agent, it will be appreciated by those skilled in the art that the antineoplastic agent may previously be coated with a coating. Coatings are discusses in more detail below The preceding description is intended to highlight variations of formulation techniques already well known in the art. However, the expanding tablets of the invention can be made by any manufacturing process. Specific novel and therapeutically useful gastric retention dosage forms are disclosed below.

Expanding tablets may be a matrix type in which the antineoplastic agent is contained in or coats the surface of particles uniformly dispersed throughout the gastric retention vehicle composition. In a matrix construction, the particles of antineoplastic agent may be a milled powder or granulate. The particles also may be pre-formulated beads, pills, pellets, microcapsules, microspheres, microgranules, nanocapsules or nanospheres and the like containing or having on their surface the antineoplastic agent, in which case these pre-formulated particles are dispersed in the matrix.

A pre-formulated particle may contain the powdered antineoplastic agent in a natural, semi-synthetic or synthetic polymer matrix. Representative matrices for dispersed particles are polysaccharides, agar, agarose, sodium alginate, carrageenan, gum arabic, tragacanth gum, locust bean gum, pectin, amylopectin, gelatin, starch, microcrystalline cellulose and hydrogels. Further particle matrices can include crosslinked gelatin, crosslinked albumin, crosslinked sodium alginate, crosslinked carboxymethylcellulose, crosslinked polyvinyl alcohol and crosslinked chitin as described in U.S. Pat. No. 5,007,790.

A pre-formulated particle may contain the antineoplastic agent in mixture with excipients that do not retard its release. Even if the particle core contains excipients that in certain applications would retard release of an active ingredient, such as high molecular weight polyvinyl pyrollidone, rapid release from a particle may occur nevertheless due to the small volume and relatively large surface area of particles.

A pre-formulated particle, e.g., bead, tiny pill, microsphere, nanosphere or microgranule, may be coated with a substance or substances that are impermeable or semipermeable to the antineoplastic agent and/or slowly dissolve in gastric fluid. Such a coating may be used to slow the release of the antineoplastic agent or to delay the release of the antineoplastic agent. A delay release coating is impermeable to the antineoplastic agent until the coating is breached by the gastric fluid. Dosage forms of the matrix type may be formulated for delayed release using coated particles, in which case the gastric retention vehicle composition will retain the dosage forms in the stomach until the delay time has passed, whereupon the drug is released.

Delayed release and sustained release particles may be coated with known film coating agents such as water soluble resins, such as arabinogalactan, carboxymethylcellulose, gelatin, gum arabic, hydroxyethylcellulose, methylcellulose, polyvinyl alcohol, polyacrylic acid, and starch; water insoluble resins, such as cellulose nitrate, ethyl cellulose, e.g., Ethocel™; cellulose nitrate, polyamide, polyethylene, poly(ethylene-vinyl acetate), poly(lactide-co-glycolide), polymethacrylate, e.g., Eudragit™ NE, Eudragit™ RS, Eudragit™ RL, Eudragit™ L and Eudragit™ S and silicones; waxes and lipids such as paraffin, carnauba wax, spermaceti, beeswax, stearic acid stearyl alcohol and glyceryl stearates; and enteric resins such as cellulose acetate phthalate, polyvinyl acetate and hydroxypropyl methylcellulose acetate. The glyceryl esters may be mixed with a wax as previously described in U.S. Pat. No. 4,764,380, which is incorporated by reference in its entirety. Such a coating may be made from triglyceryl esters like glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodecenoate, glyceryl didecenoate and glyceryl tridecenoate. Waxes that may be used include beeswax, cetyl palmitate, spermacetic wax, carnauba wax, cetyl myristate, cetyl palmitate, ceryl cerotate, stearyl palmitate, stearyl myristate and lauryl laurate. Particles coatings may also be from other polymeric coating substances which include methylcellulose phthalate, poly(alkyl methacrylates), poly(alkyl cyanoacrylates), polyglutaraldehyde, poly(lactide-glycolide) and albumin. Additional coating materials that may be used are disclosed in U.S. Pat. Nos. 4,434,153; 4,721,613; 4,853,229; 2,996,431; 3,139,383 and 4,752,470, which are hereby incorporated by reference in their entirety.

Pre-formulated particles coated with delayed release coatings may be advantageously used to produce an expanding tablet or capsule for pulsed release of the antineoplastic agent. Gastric fluid rapidly penetrates the expanding dosage form because of the hydrophilicity and porosity of the preferred gastric retention vehicle compositions.

Consequently, the coated particles contact gastric fluid approximately simultaneously regardless of their proximity to the outer surface of the dosage form. One can deliver two, three (or more) timed doses in a pulse fashion while the patient needs to take the dose only once. For this purpose, particles may be provided with coatings of different thicknesses. Alternatively, the particles may be coated with different substances having different dissolution rates in gastric fluid. The coatings of a certain proportion of particles, either those with a thin coating or a relatively soluble coating, are breached nearly simultaneously. This causes release of the antineoplastic agents from those particles over a short time period, i.e., in a pulse. A second pulse occurs when the coating of particles having either a thicker coating or a coating of a slower dissolving substance is breached. A third pulse occurs when particles having a coating that is either yet thicker or formed of a yet less soluble substance is breached. The timing and intensity of the pulses can be determined by the formulator using knowledge available about the dissolution rates of coating substances and by routinely selecting the proportion of each type of coated particle to match the intensity of the pulse desired. The three doses would mimic taking multiple doses of the antineoplastic agent at the prescribed times, with the antineoplastic agent being absorbed from the stomach or upper intestine with each dose. Such dosing allows for improved compliance to dosage schedules and in many cases will lead to improved therapy. Pulsed release dosage forms that do not include gastric retention will deliver each pulse in a different part of the GI tract with different absorption profiles for each of the doses. Such therapy would not be equivalent to taking three doses of the antineoplastic agent at the prescribed times, wherein the antineoplastic agent would have been absorbed from the stomach or upper intestine in each case.

In a hydrated state, the gastric retention vehicle compositions of this invention do not necessarily limit diffusion of a solubilized antineoplastic agent into the gastric environment. Therefore, the pulsed release of antineoplastic agent inside of the expanded tablet may translate into pulsed release into the gastric fluid.

Expanding tablets also may contain the antineoplastic agent in a reservoir (or depot) adjacent to, at least partially surrounding or at least partially surrounded by the gastric retention vehicle composition. Reservoir forms may contain the antineoplastic agent in a reservoir that is embedded in a shell of any desired thickness that does not cause the dosage form to be too large to be swallowed by the patient. Embedded tablets and tablets with cores are examples of reservoir type of dosage forms. A reservoir type further includes capsule forms, multilayer forms and other forms wherein the antineoplastic agent is separated from the expanding composition. The reservoir may be fully embedded in a shell of the expanding composition or it may be partially embedded so that a portion of the surface of the reservoir is exposed. A reservoir may be a tablet enclosed within a capsule along with a tablet containing the expanding composition. These types of products may be manufactured using methods known in the art, while novel and particular preferred embodiments of reservoir dosage forms are described below.

The reservoir may be formulated to be either immediate release or controlled release. The release profile of the dosage form may be made to approximate the release profile of the reservoir (even when the reservoir is completely embedded in a shell) because the hydrated and expanded composition does not necessarily inhibit diffusion of solubilized substances into the gastric environment. For example, an immediate release reservoir may be prepared by blending the antineoplastic agent with microcrystalline cellulose, lactose and magnesium stearate and compressing the blend into a compacted reservoir. For another example, a sustained release reservoir may be prepared by direct compression of the antineoplastic agent with about 5–75% hydroxypropyl methylcellulose, such as Methocel® K15M, K100LV, K4M, K100M, E4M and E10M, lactose and magnesium stearate.

A reservoir may be coated with a conventional sustained release coating. Such coating materials include polymethacrylate, e.g., Eudragit™ NE, Eudragit™ RS, Eudragit™ RL, Eudragit™ L, Eudragit™ S, and mixtures of hydrophilic and hydrophobic film forming agents. Hydrophilic film formers include methyl cellulose, hydroxypropyl methylcellulose, cellulose phthalate, cellulose acetate phthalate and polyvinyl alcohol. Hydrophobic film forming agents include ethyl cellulose, cellulose acetate, hydroxypropyl methylcellulose phthalate, polyvinyl alcohol maleic anhydride copolymers, β-pinene polymers rosin, partially hydrogenated rosin and glycerol esters of rosin. A sustained release coating may be applied by methods known in the art such as by fluid bed or pan coating techniques.

In addition to being of an immediate release or sustained release nature, the reservoir can further be of a delayed pulse release nature or a delayed-sustained release nature. For instance, the antineoplastic agent may also be contained in tablets that are either partially embedded in the gastric retention vehicle composition or attached thereto by an adhesive. These tablets can be of a slow release nature giving slow or controlled release for an extended period of time in the stomach. These tablets can further be of a delayed pulse release nature. The expanding composition of this invention will retain these forms in the stomach until the delay time has passed whereupon the drug will be released in a burst or pulse fashion. Attaching or partially embedding several such tablets, each timed with a different delay to release, to the composition of this invention allows versatile dosing schemes from one taken dose. For example one could deliver three (or more) timed doses in a pulse fashion while the patient needs to take the dose only once. The three doses would mimic taking three doses of the drug at the prescribed times, with the drug being absorbed from the stomach with each dose. Such dosing allows for improved compliance to dosage schedules and in many cases will lead thereby to improved therapy. Delayed dosage forms that are not coupled to gastric retention will deliver each such dose in a different part of the GI tract with different absorption profiles for each of the doses. Such therapy would not be equivalent to taking three doses of the drug at the prescribed times, wherein the drug would have been absorbed from the stomach in each case.

The reservoir may also be attached to the expanding composition with an adhesive. The gastric retention vehicle composition is compacted into a tablet ("GRDS tablet,"). The reservoir can be attached by adhesive during manufacture by depositing a drop of adhesive on a GRDS tablet as it leaves the punch station in the tableting machine and having a device push the reservoir, e.g., another tablet, containing the drug against the deposited adhesive.

Expanding tablets may also have a layered construction wherein the antineoplastic agent, alone or in mixture with any other excipients, form a layer that is bonded, e.g., by compression, to another layer containing the expanding composition. Preferred dimensions for a layered dosage form are about 14×8 mm±2 mm. A layered construction may be prepared by conventional multilayer compression techniques. A layered dosage form comprising two or more layers, one comprising the expanding composition and another comprising the antineoplastic agent and any other desired excipients, may be made to delay release of the antineoplastic agent by coating only the antineoplastic agent-containing layer with a conventional coating resistant to gastric fluids. A further method of achieving a delay in the release is to formulate the drug-containing layer as a matrix that delays diffusion and erosion or by incorporating the antineoplastic agent in microcapsules or coated beads within the drug-containing layer.

Another solid dosage form is a capsule. The capsule shell may be any conventional shell (e.g. gelatin) that degrades in gastric fluid to release a capsule filling. The capsule filling comprises a powder blend or granulate (as previously described) or tablet containing the gastric retention vehicle composition, antineoplastic agent and, optionally, other excipients. Capsules exhibit a similar rate and extent of expansion as tablets and are retained in the stomach for a comparable time period. There is, however, a delay in the commencement of expansion for the time required for degradation of the capsule shell to allow gastric fluid to contact the gastric retention vehicle composition.

In an especially preferred capsule embodiment, the capsule encloses a tablet (or other reservoir) containing the antineoplastic agent and a GRDS tablet. The two tablets can be adhered to each other in situ the stomach by coating a side of one of the tablets that faces the other tablet with an aqueous based adhesive. The tablets are loaded into an appropriately sized gelatin capsule where the tablets are in physical contact. When water enters the capsule, the adhesive is wetted and adheres the tablets together due to their proximity in the capsule prior to the rapid swelling of the GRDS tablet. The tablets remain adhered to each other after the swelling. Preferred water based adhesives for this use are protein adhesives such as gelatin, egg albumin, and casein, their salts and derivatives and polysaccharide adhesives such as starch, modified starches, and other polysaccharide derivatives known in the art as glues. The most preferred adhesive for in situ adhesion of the drug reservoir to a GRDS tablet is sodium caseinate, which is available commercially as Emulac™ 50.

Solid dosage forms of this invention may be made in any shape desired. Ovoid or elliptical shaped tablets are well retained in human patients after expanding to their full extent. An ovoid or elliptical dosage form preferably is sized at between about 4 mm and 10 mm in two dimensions and between about 10 mm and 20 mm in the third dimension, more preferably 6×6×16 mm±2 mm.

Solid dosage forms of this invention can be retained in the stomach for three hours or more, more preferably about five hours or more. The dosage forms of the present invention are capable of expanding in volume by a factor of about three or more, about five or more if an gastric retention vehicle composition according to the preferred embodiments is used and, about eight or more if an gastric retention vehicle composition according to the most preferred embodiments is used. Expansion occurs within about fifteen minutes of contacting gastric fluid, within about five minutes when formulated according to the preferred embodiments. Over time, the swollen dosage form degrades into particles that are sufficiently small to traverse the pylorus.

Further improvement in gastric residence time may be realized by adding an effervescent compound to the gastric retention vehicle composition that produces gas when contacted with gastric fluid, such as sodium bicarbonate. In a dry granulation process, the effervescent compound may be introduced into the dosage form by blending it into the gastric retention vehicle composition before or after first compaction. In a wet granulation process, it may be provided as an extragranular constituent after wet granulation. Further, the effervescent compound may be a constituent of a reservoir in reservoir-type dosage form. The effervescent compound is preferably used at low concentration, i.e. from about 0.5 wt % to about 5 wt. % of the dosage form. In addition to sodium bicarbonate, effervescent compounds include, for example, other alkali and alkaline-earth metal carbonates and bicarbonates.

Mucoadhesive substances also may be added to enhance gastric retention of dosage forms prepared according to the present invention.

In another aspect, the present invention provides liquid compositions for gastric delivery of antineoplastic agents. In the liquid form embodiments of the invention, the antineoplastic agent is dissolved or dispersed in a gastric retention vehicle composition comprising a gelling agent. The liquid pharmaceutical composition may be a solution, suspension, or syrup.

The gastric retention properties of the liquid pharmaceutical composition are afforded by gelling, precipitation or coacervation of the gelling agent in the stomach. The gel, precipitate or coacervate that forms in the patient's stomach traps the drug in the stomach for an extended gastric delivery. The gelling agent may be activated by a change in pH or change in temperature. The gelling agent may contain a synthetic polymer, a polysaccharide, a protein or a coacervate of a protein and a polysaccharide as a gelling agent. Examples of such delivery systems are known in the art but have not been suggested as being useful for the oral systemic delivery of antineoplastic agents. Cox, G., "Pectin Liquid Compositions," WO 96/29055; Bogentoft, C., "Gel-forming, Liquid Carrier Compositions, and Their Use in Pharmaceutical Dosage Forms," WO 92/09307; Zatz, J. L.; Woodford, D. W., "Oral Controlled Release Liquid Pharmaceutical Which Forms Gelatinous Matrix in the Stomach," U.S. Pat. No. 4,717,713. U.S. Pat. No. 4,717,713 and International Publications WO 96/29055 and WO 92/09307 are hereby incorporated by reference in their entirety.

A gelling agent of the liquid pharmaceutical composition may be based upon coacervation brought about by exposure to low pH. One such system is a mixture of ethyl hydroxyethylcellulose (EHEC) and a surfactant.

Suitable surfactants are cationic surfactants and anionic surfactants that do not protonate at gastric pH. Suitable surfactants include hexadecyltrimethylammonium chloride, tetradecylbetainate chloride and hexadecylpyridinium chloride, sodium dodecyl sulfate, sodium dodecyl monoethyleneoxide sulfate, sodium dodecyl sulfonate, sodium dosdecyl phosphate, sodium doecyl phosphonate, sodium p-dodecylbenzene sulfonate to name just a few. Other surfactants may be used so long as they engage in a strong hydrophobic interaction with ethylhydroxyethylcellulose in aqueous solution at gastric pH.

The total concentration of a EHEC/surfactant system is preferably in the range of 0.5–3 wt. %, more preferably from about 0.5 to 1.5 wt. %. EHEC is used in approximately 5 to 25 fold excess over the surfactant, by weight.

Another pH activated gelling agent is a mixture of a low methoxylated pectin and a divalent metal salt, like calcium carbonate, that is coated with a substance that dissolves upon contact with acid. Release of the metal salt in the patient's stomach causes the cation to engage in crosslinking interactions with the pectin molecules so as to form a gelatinous network and, in the case of carbonate salt, produces gas bubbles which are entrapped in the gelatinous network. Preferred methoxylated pectins have 20–50% degree of methoxylation, preferably from about 30–40% degree of methoxylation and a degree of amidation of from about 3% to about 23%. This system may be used to deliver antineoplastic agents according to the present invention either with the effervescent aspect or without the effervescent aspect by using a non effervescent calcium salt anion such as stearyl.

The gelling agent may be activated by increased temperature. Methylcellulose forms aqueous dispersions that are flowable below body temperature but which become viscous with increased temperature. At body temperature, a dispersion of 5 wt. % or above of methylcellulose in water forms a gel of sufficient mechanical resilience to be retained in the stomach.

Yet other operative gelling systems include a mixture of from about 0.5 to about 4 weight percent sodium alginate, 0.5 to about 3 weight percent or less of xanthan gum, carrageenan or gelatin.

In addition to the substances previously discussed which enable gastric retention, the solid and liquid form gastric retention vehicle compositions may contain other excipients which may be added for a variety of purposes. It will be understood by those in the art that some substances serve more than one purpose in a pharmaceutical composition. For instance, some substances are binders that help hold a tablet together after compression, yet are disintegrants that help break the tablet apart once it reaches a patient's stomach. It will be further understood that the hydrogel, superdisintegrant and tannic acid of the most preferred solid form gastric retention vehicle composition may perform additional functions in the dosage form, which functions may already be known to those skilled in the art.

Additional excipients that may be added include diluents. Diluents increase the bulk of a pharmaceutical dosage form making it easier for the patient and caregiver to handle. Diluents for solid dosage forms include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of a powder composition or granulate and improve the accuracy of dosing. Excipients that may function as glidants include colloidal silicon dixoide, magnesium trisilicate, powdered cellulose, starch, talc and tribasic calcium phosphate.

A tablet is made by compressing a powder composition granulate between a punch and dye. Some excipients and active ingredients have a tendancy to adhere to the surfaces of the punch and dye, which can cause the tablet to have pitting and other surface irregularities. A lubricant may be added to the composition to reduce adhesion and ease release of the product form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Liquid pharmaceutical compositions will contain a solvent such as corn syrup, water, glycol, glycerin, propylene glycol, vegetable oils and alcohols.

Liquid pharmaceutical compositions may contain emulsifying agents to disperse a poorly soluble antineoplastic agent or an excipient uniformly throughout the composition. Emulsifying agents that may be useful in liquid pharmaceutical compositions of the present invention include, for example, lecithin, sorbitan monoleate, gelatin, egg yolk, casein, cholesterol, acacia, tragacanth, chondrus, pectin, methyl cellulose, carbomer, cetostearyl alcohol and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition according to the present invention may also contain a buffer such as guconic acid, lactic acid, citric acid or acetic acid, sodium guconate, sodium lactate, sodium citrate or sodium acetate.

Flavoring agents and flavor enhancers make the solid dosage forms and liquid pharmaceutical compositions more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid. Sweetening agents such as sorbitol, saccharin, sodium saccharin, sucrose, aspartame, fructose, mannitol and invert sugar may be added to improve the taste.

Solid and liquid compositions may also be dyed using any pharmaceutically acceptable colorant to improve their appearance and/or facilitate patient identification of the product and unit dosage level.

Selection of additional excipients and the amounts to use may be readily determined by the formulation scientist based upon experience and consideration of standard procedures and reference works in the field.

A unit dose of irinotecan in one of the dosage forms of the present invention, e.g. one tablet or capsule of a solid form or an ingestible volume, like a tablespoon of syrup, of a liquid form preferably is dosed with from about 20 to about 250 mg of irinotecan, more preferably from about 20 to about 40 mg of irinotecan.

A unit dose of etoposide in one of the forms of the present invention preferably contains from about 25 to about 250 mg of etoposide, more preferably from about 25 to about 75 mg of etoposide, and yet more preferably from about 25 to about 50 mg.

A unit dose of paclitaxel in one of the forms of the present invention preferably contains from about 25 to about 250 mg of paclitaxel and more preferably from about 25 to about 100 mg of paclitaxel.

Having thus described the present invention with reference to certain preferred embodiments, the following non-limiting examples are provided to further illustrate the invention.

EXAMPLES

Materials

The HPMC used was Methocel® K-15PM, available from Dow Chemical Co. The hydroxypropyl cellulose used was Klucel® HF NF, available from Hercules, except where otherwise indicated. The croscarmellose sodium used was Ac-Di-Sol® available from Avebe Corp. The crosslinked polyacrylic acid was Carbopol® 974P available from B.F. Goodrich Chemical Ltd. Tannic Acid was purchased from Merck. All materials were pharmaceutical grade.

Example 1

Degree of Swelling of Illustrative Solid Gastric Retention Delivery Systems

The compositions of each of the tablets prepared in Example 1 are summarized in Table 1. All the compositions contain HPMC, tannic acid, a superdisintegrant and 1% magnesium stearate. All of the excipients, except for magnesium stearate, were mixed simultaneously and thoroughly blended by hand. Magnesium stearate was then added at a level of 1% w/w and the blend was further mixed by hand until the magnesium stearate was uniformly distributed throughout the composition. The amount of each composition needed to produce a 5 mm thick tablet was determined and then that amount was compressed into 5 mm thick tablets on a Manesty f3 single punch tableting machine with a 10 mm diameter punch and die. Tablets ranged in weight from 350–400 mg and each had a hardness within the range of 5–7 KP as tested in an Erweka hardness tester.

The tablets were added to 40 ml of simulated gastric fluid (0.1 M HCl) contained in a 50 ml beaker and maintained at 37±2° C. The tablets were removed after fifteen minutes with a tweezers and measured with a caliper. Gel strength was assessed qualitatively with the tweezers.

The results of the degree of swelling tests are summarized in Table 2. Expansion of the hydrogel was increased using either croscarmellose sodium or sodium starch glycolate. The formulation can optionally and advantageously contain a mixture of two hydrogel polymers as demonstrated by the incorporation hydroxypropyl cellulose and Carbopol® in the formulations of Examples 5, 6 and 8. The tablet that expanded the most (36 fold) contained about 5 wt. % tannic acid and croscarmellose sodium as the superdisintegrant. The tablet with the second highest expansion (18 fold) also contained about 5 wt. % tannic acid but used sodium starch glycolate as the superdisintegrant. Both of those gels (Examples 1 and 4) were qualitatively weak compared to those of examples 5–8. The best performing tablets in terms of a high degree of expansion and good mechanical strength are those of Examples 5 and 8, which contained 5 wt. % tannic acid and used both hydroxypropyl methylcellulose and hydroxypropyl cellulose hydrogel polymers.

TABLE 2

| Formulation No. | Degree of Swelling[a] | Strength |
|---|---|---|
| 1 | 18.1 | moderate |
| 2 | 12.7 | moderate |
| 3 | 7.2 | moderate |
| 4 | 36.0 | moderate |
| 5 | 10.4 | strong |
| 6 | 2.0 | strong |
| 7 | 4.5 | strong |
| 8 | 9.7 | strong |

[a]ratio of hydrated tablet volume to dry tablet volume

Example 2

Rate of Swelling of Illustrative Solid Gastric Retention Vehicle Compositions

The formulations in Table 3, below, were prepared by first dry mixing the powdered ingredients, except the magnesium stearate, for 5 minutes. Magnesium stearate was then added and blended in over 2 minutes. The formulation was pressed into oval tablets of dimensions 17×9×8.5 mm using a Manesty f3 single punch tablet press where the 8.5 is the tablet thickness or height in the dimension of compression.

TABLE 1

GRDS Formulations for Degree of Swelling Tests

| | Formulation No. (wt. %) | | | | | | | |
|---|---|---|---|---|---|---|---|---|
| Excipient | 1 | 2 | 3 | 4 | 5 | 6 | 7 | 8 |
| Hydroxypropyl methylcellulose | 23.8 | 32.7 | 30.3 | 23.8 | 26.7 | 38.5 | 34.8 | 15.9 |
| Hydroxypropyl cellulose | 0.0 | 0.0 | 0.0 | 0.0 | 16.0 | 19.2 | 0.0 | 47.6 |
| Cross-linked polyacrylic acid | 0.0 | 0.0 | 0.0 | 0.0 | 0.0 | 0.0 | 8.7 | 0.0 |
| Total hydrogel | 23.8 | 32.7 | 30.3 | 23.8 | 42.7 | 57.7 | 43.5 | 63.5 |
| Sodium starch glycolate | 71.4 | 65.4 | 60.6 | 0.0 | 53.3 | 38.5 | 52.2 | 31.7 |
| Croscarmellose sodium | 0.0 | 0.0 | 0.0 | 71.4 | 0.0 | 0.0 | 0.0 | 0.0 |
| Tannic acid | 4.8 | 2.0 | 9.1 | 4.8 | 4.0 | 3.8 | 4.3 | 4.8 |
| Total | 100 | 100 | 100 | 100 | 100 | 100 | 100 | 100 |

TABLE 3

GRDS Formulations for Rate of Swelling Tests

| Ingredient | Formulation No. (wt. %) | | |
|---|---|---|---|
| | 10 | 11 | 12 |
| HPMC K15 | 16 | 15.7 | 13.4 |
| HPC | 48 | 47.2 | 45 |
| Croscarmellose sodium | 31.9 | 31.4 | 29.1 |
| Tannic acid | 3.1 | 4.7 | 12 |
| Magnesium stearate | 1 | 1 | 0.5 |

The tablets were immersed in 450 ml of USP Gastric TS buffer (pH=1.2) without enzymes at 37° C. in a USP type II dissolution bath with the paddles set at the top of the buffer so as not to hit the expanding tablets. The solution was stirred at 50 RPM. The tablets were removed from the buffer at 15 minutes, 1 and 3 hours, gently blotted dry with paper, and measured using a calibrated caliper. The two major dimensions, length and height, were measured. The third dimension expanded from 9 mm to about 14 mm in all of the cases. Results of the measurements are shown in Table 4.

TABLE 4

Rate and Degreee of Swelling of GRDS tablets in USP Gastric TS buffer

| Formulation No.: | 10 | 11 | 12 |
|---|---|---|---|
| Time (hours) | Size (mm × mm) | Size (mm × mm) | Size (mm × mm) |
| 0 | 17 × 8.5 | 17 × 8.5 | 17 × 8.5 |
| 0.25 | 21 × 15 | 25 × 21 | 25 × 18 |
| 1 | 21 × 15 | 32 × 24 | 27 × 19 |
| 3 | 21 × 15 | 32 × 24 | 27 × 20 |

Most of the expansion occurred in the first 15 minutes. One can see that the degree of expansion was greatest in the dimension of compression. This dimension expanded between 1.8 and 2.8 times its size. In length, the tablet grew from 1.2 to 1.9 times its size.

Example 3

Effect of GRDS Composition on Gel Strength

Method

Gel strength was measured by the weight needed to deflect the expanded gel by 4 mm. The gels were removed from the Gastric TS buffer, blotted dry with paper, and placed on a flat surface on a top loading balance. A plastic cylinder was placed on the gel and water was added slowly to the cylinder until the gel was compressed downward by 4 mm. The weight required for 4 mm deflection was recorded.

Effect of Tannic Acid Content on Gel Strength

Formulations were prepared as in Example 2 with varying amounts of tannic acid. Tablets were pressed and immersed in simulated gastric fluid as described in Example 2. All the tablets swelled to at least 25×22 mm in 15 minutes. Results of the measurement of gel strength are found in Table 5.

TABLE 5

Strength of Expanded Gels as a Function of Tannic Acid Content

| Formulation | % Tannic Acid | Strength (g) |
|---|---|---|
| 13 | 4.2 | 27 |
| 14 | 4.7 | 51 |
| 15 | 6 | 90 |
| 16 | 7 | 147 |

Raising the percent of tannic acid from 4.2 to 7 percent dramatically increased the strength the expanded gel. In experiments not reported in Table 5 it was discovered that increasing the percent of tannic acid from 7 and 12% resulted in little further increase in gel strength.

Effect of Superdisintegrant Content on Gel Strength

Formulations were prepared as described in Example 2 with varying amounts of croscarmellose sodium. Tablets were pressed and the tablets were immersed in simulated gastric fluid as described in Example 2. All the tablets swelled to at least 23×18 mm in 15 minutes. The formulations tested and the results of the measurement of gel strength are provided in Table 6.

TABLE 6

Strength of Expanded Gels as a Function of Croscarmellose Sodium Content

| Ingredient | Formulation No. (wt. %) | | |
|---|---|---|---|
| | 17 | 18 | 19 |
| HPC | 46.6 | 50 | 55.9 |
| Croscarmellose sodium | 31 | 26 | 21.4 |
| HPMC K15 | 15.5 | 15 | 15.7 |
| Tannic acid | 5.9 | 6 | 6 |
| Magnesium stearate | 1 | 1 | 1 |
| Weight required to deflect gel by 4 mm (g) | 90 | 116 | 157 |

As can be seen in Table 6, lowering the percent of the superdisintegrant in the formulation tended to increase the gel strength.

Example 4

Gastric Retention Delivery System with In Situ External Tablet Adhesion

One method of obtaining pulsed delivery of a drug in the stomach is to attach tablets with predetermined delays before disintegration to the gastric retention delivery system (GRDS) tablet. Such attachment can be through partial embedding of the tablet in the GRDS matrix or by adhering it externally to the GRDS. In this example we show the feasibility of such external adhesion.

The GRDS formulation was that shown in Table 7.

TABLE 7

| Ingredient | Weight Percent |
|---|---|
| HPC | 50.3 |
| HPMC | 16.7 |
| Croscarmellose Sodium | 22 |
| Tannic Acid | 10.0 |
| Magnesium Stearate | 1.0 |

The powders, except the lubricant, were mixed for five minutes. Magnesium stearate was then added and the powders mixed for one minute more. The blend was pressed into rectangular (truncated oval) tablets of 10×7×7 mm in a Manesty f3 single punch tableting machine.

An adhesive solution was prepared as follows. Sodium caseinate (Emolac™ 50, 15 g) was dissolved in 100 ml water by stirring overnight at room temperature. 500 ml of ethanol was added with stirring to obtain an emulsion of 2.5% sodium caseinate in water:ethanol.

The tablets were then coated with the adhesive. The emulsion was spray coated on the tablets in a pan coater at a rate of 4 ml /min with the product temperature between 30–40° C. to a coating weight of between 5 and 14 mg. The tablets were air dried in the coating pan to give GRDS tablets coated with the adhesive.

Placebo tablets based on microcrystalline cellulose were prepared (5×5×5 mm rectangular) and coated with Eudragit™ S to make them impervious to acid conditions. The tablets were loaded into a gelatin #00 capsule in a stack such that a GRDS tablet was in between two placebo tablets. The contact between the tablets was on the 7×7 mm face of the GRDS tablet which is perpendicular to the compression axis.

The gelatin capsules were placed in 0.1 N HCl in a USP type II dissolution bath at 37° C. and stirred at 50 RPM. The capsule dissolved and the three tablet stack adhered to one another in situ. Within 15 minutes the GRDS tablet had swollen to 13×22 mm from 10×7 mm (the swelling being mostly along the compression axis). At two hours the GRDS tablet had swollen to 14×25 mm. The placebo tablets remained attached to the GRDS tablet, despite its swelling, for over 12 hours in the dissolution bath. In order to test the viability of the adherence under more vigorous conditions of flow, the stack was placed in 0.1 N HCl at 37° C. in a disintegration tester at 50 strokes per minute. The flows on the tablets in a disintegration tester are considerably stronger than in the dissolution tester. The three tablets remained adhered to one another for 10 hours.

Example 5

Solid Dosage Forms for Gastric Delivery of Antineoplastic Agents

An antineoplastic agent can be formulated with the GRDS system in several ways. It can be dispersed homogeneously throughout the formulation. It can be formulated into a separate tablet that is embedded into the GRDS matrix. It can be formulated as a separate layer and a bilayer GRDS formed. Irinotecan is delivered by controlled release in each of the formulations below while the GRDS portion has swelled greatly to afford gastric retention. Each form has its advantages. The dispersed tablet has the advantage of ease of manufacture. It, however, has less flexibility in formulative control over the rate of release since most of the excipients in the matrix are dictated by its GRDS nature. The embedded tablet and the bilayer tablet are somewhat more complicated to form, necessitating special commercial equipment for both embedding tablets and for bilayer tablets, but they offer the advantage of full freedom in formulating the drug layer, thereby allowing a greater measure of control for the drug release profile.

1) Irinotecan Dispersed Homogeneously Throughout the GRDS

Tablets containing irinotecan were made by direct compression. The formulations made are given in Table 8. All the components except the magnesium stearate were blended manually for three minutes. Magnesium stearate was added and the blend mixed for a further minute. The blend was then pressed into 850 mg tablets in a Korsch 6 punch press using oval punches of dimension 16×8 mm.

TABLE 8

Formulations of Irinotecan Homogeneously Dispersed in a GRDS Matrix

| Ingredient | Formulation No. (wt. %) | | |
|---|---|---|---|
| | 20 | 21 | 22 |
| Irinotecan | 7.1 | 7.1 | 7.1 |
| HPC HF | 55.6 | 47.6 | 49.8 |
| Croscarmellose sodium | 11.5 | 23.1 | 17.3 |
| HPMC K15M | 15.9 | 13.6 | 15.9 |
| Tannic Acid | 9.4 | 8.1 | 9.4 |
| Magnesium Stearate | 0.5 | 0.5 | 0.5 |

The tablets were tested for swelling and gel strength as described above in Example 2. The tablets were further tested for drug release in simulated gastric test solution in a USP type II dissolution bath at 37° C. with a paddle speed of 50 RPM. The results of these tests are given in Table 9.

TABLE 9

Swelling and Dissolution of Irinotecan in Dispersed GRDS Tablets

| Characteristic | Time (hr) | Formulation No. | | |
|---|---|---|---|---|
| | | 20 | 21 | 22 |
| Dimensions (length × height) (mm) | 1 | 21.3 × 14.4 | 31.1 × 28.0 | 28.4 × 26.3 |
| | 3 | 22.9 × 16.3 | 30.9 × 29.1 | 29.0 × 26.7 |
| | 6 | 23.8 × 19.0 | 32.1 × 29.1 | 28.9 × 28.3 |
| Water uptake (g) | 1 | 1.4 | 8.9 | 7.6 |
| | 3 | 2.3 | 9.6 | 7.7 |
| | 6 | 3 | 9.6 | 7.7 |
| Gel Strength (g) | 1 | 1188 | 105 | 106 |
| | 3 | 801 | 101 | 161 |
| | 6 | 554 | 101 | 193 |
| Percent Release of Irinotecan | 2 | 0 | 18 | 7 |
| | 4 | 1 | 31 | 11 |
| | 6 | 2 | 43 | 16 |
| | 8 | 4 | 54 | 20 |

2) Irinotecan in a Tablet Partially Embedded in the GRDS

Irinotecan and the excipients in Table 10 were granulated with water, dried and milled. Magnesium Stearate (0.5%) was added and the blend mixed for one minute. Tablets of diameter 6 mm weighing 85 mg were produced in a Korsch 6 punch rotary tablet machine. The formulations tested are given in Table 10.

TABLE 10

Formulations of Inner Irinotecan Tablet

| Ingredient | Formulation No. (wt. %) | |
|---|---|---|
| | 23 | 24 |
| Irinotecan | 70 | 70 |
| Lactose | 25 | 0 |
| Mannitol | 0 | 20 |
| HPMC K100LV | 5 | 10 |

These core tablets were coated with a thin coat (~10µ) layer of Eudragit E, a methacrylate polymer that is readily soluble in acidic environments. The core tablets were then embedded at the surface of a GRDS matrix tablet whose composition is shown in Table 11.

TABLE 11

GRDS Composition of Formulations Nos. 23 and 24

| Ingredient | Weight Percent |
| --- | --- |
| Croscarmellose sodium | 22.0 |
| HPC HF | 50.3 |
| HPMC K15M | 16.7 |
| Tannic Acid | 10.0 |
| Magnesium stearate | 1.0 |

The tablets expanded readily in gastric TS solution with a water uptake of at least 6 grams. These tablets were tested for drug release as described above. The results are given in Table 12.

TABLE 12

Cumulative Percent Release of Drug from Embedded Tablets

| | Percent Release | |
| --- | --- | --- |
| Time (hr) | 23 | 24 |
| 0 | 0 | 0 |
| 1 | 6 | 3 |
| 2 | 14 | 7 |
| 4 | 63 | 27 |
| 8 | 87 | 73 |

3) Irinotecan as a Separate Layer—Bilayer GRDS

Irinotecan was granulated with about 10% of the HPMC and half the mannitol using water as the granulation liquid. After drying and milling, the granulate was blended with the croscarmellose sodium, the remaining HPMC and mannitol and subsequently with the magnesium stearate for a final formulation as shown in Table 13.

TABLE 13

Composition of Irinotecan-Containing Layer of Bilayer Tablet

| Ingredient | Weight Percent |
| --- | --- |
| Irinotecan | 30 |
| HPMC K100LV | 27 |
| Mannitol | 23 |
| Croscarmellose sodium | 20 |
| Magnesium stearate | 0.3 |

The GRDS layer was made by blending the following ingredients:

TABLE 14

Composition of GRDS Layer of Bilayer Tablet

| Ingredient | Weight Percent |
| --- | --- |
| Croscarmellose sodium | 20 |
| HPC HF | 52 |
| HPMC K15M | 17 |
| Tannic Acid | 10 |
| Magnesium Stearate | 1 |

The GRDS blend, 800 mg, was fed into the die of a 16×8 mm oval punch. The irinotecan blend, 200 mg, was added as a separate layer over the GRDS blend. The entire assembly was pressed into a bilayer tablet. The tablets showed proper swelling properties and were tested for drug release in a USP type II dissolution apparatus as described above. The results of the drug release are shown in Table 15.

TABLE 15

Cumulative Percent Release of Drug from Bilayer Tablets

| Time (h) | Percent Release |
| --- | --- |
| 0 | 0 |
| 1 | 33 |
| 2 | 49 |
| 4 | 85 |
| 8 | 98 |

Example 6

Enhanced Systemic Delivery of Irinotecan and SN-38 by Gastric Absorption of Irinotecan in the Beagle Dog Introduction Six dogs are used in a 3 way crossover study to determine the area under the curve ("AUC") of bloodstream concentration versus time after oral administration of irinotecan in a GRDS tablet and after an i.v. dosing of the drug. Blood samples are taken at predetermined intervals and the concentration of irinotecan lactone, irinotecan carboxylate, SN-38 lactone and SN-38 carboxylate are determined by HPLC methods. SN-38 is the active metabolite of irinotecan and only the lactone form is active. A plot of plasma concentration against time allows calculation of the area under the curves and the relative bioavailability of the various forms of the drug. Enhancement in the percentage of the lactone form of SN-38 when dosing orally with a GRDS formulation makes oral dosing a viable alternative to i.v. dosing.

Blood Sampling for Pharmacokinetic Evaluation

Prior to the study, an adequate amount (5–10 ml) of whole blood is drawn from each dog. The blood is used to prepare the standard calibration reference curve. At the study, the foreleg (right or left, as deemed appropriate by the animal handler), is shaved using an electric shaver, and the area cleansed with a chlorhexidine swab. A permanent in-dwelling polyethylene catheter is inserted using a 23 gauge needle in the cephalic vein in the foreleg of each dog and taped in place to allow for periodic blood sampling over 12 hours. A plastic bonnet is placed around the head of each dog to ensure that the dog's mouth cannot reach the catheter site.

At each time point, 2.0 ml blood is removed by syringe and then placed into a pre-labeled heparinized test tube. The test-tube is immediately centrifuged and extracted with cold methanol to prevent equilibration between the lactone and the carboxylate forms of the two drugs after the blood has been drawn. The concentration of the components are measured using literature HPLC methods. See Drengler, R. L. et. al., "Phase I and Pharmacokinetic Trial of Oral Irinotecan Administered Daily for 5 Days Every 3 Weeks in Patients with Solid Tumors", *Journal of Clinical Oncology* (1999), 17, 685–696.

The Study

The dogs are fasted overnight for a period of at least 12 hours at which time they receive a single mixed meal of solid food and liquid nutrients. 250 grams of bite-size commercial dog chow (Bonzo Feed®) are measured and placed in a feeding dish. The dog is allowed to eat over ½ hour, at which time the dish is removed. The food remaining in the dish is measured and the difference from the original 250 grams is recorded as the amount of food consumed. Additionally, 250 calories of liquid nutrients (Ensure®, 237 ml) are administered via a gastroesophageal feeding tube. No additional food is allowed for the duration of the study, but water is provided ad libitum from a tap in the dog's cage during the study.

Prior to dosing, the dog is prepared for catheter insertion and a "pre-dosing" "0" hour blood sample is drawn. The blood is drawn and the sample handled as described above.

Two hours after the meal, the dog is dosed with the test tablet. After administering the test tablet, 300 ml of pH regulated (pH 2.0) water is administered by flexible tubing to the stomach. Every hour following dosing, up to 12 hours, a sample (2 ml) of whole blood is withdrawn from the catheter and placed in a heparinized glass test-tube. The blood samples are centrifuged immediately and extracted with cold methanol. The methanol samples are analyzed by HPLC.

Results

The following ratios may be derived from the HPLC results of tests in which irinotecan is administered orally in a gastric retention dosage form and in which the drug is administered intravenously.

$$\frac{A^{GR}_{lactone}}{A^{GR}_{Total}}, \frac{A^{GR}_{Total}}{A^{IV}_{Total}} \text{ and } \frac{A^{IV}_{Total}}{A^{IV}_{lactone}}.$$

Quantity "A" is the total area under the bloodstream concentration curve over time. Superscript "GR" refers to results of a test in which irinotecan was administered in a gastric retention dosage form according to the invention and superscript "IV" refers to results of a test in which irinotecan was administered intravenously. Superscript "Oral" is used below to refer to results of a test in which irinotecan was administered in a conventional, non-gastric retention dosage form.

$A_{Total}=A_{Lactone}+A_{Carboxylate}$ is the sum of the areas under the curve of lactone and carboxylate forms of the species.

These ratios are useful for calculating the relative bioavailability of active form irinotecan and SN-38 by different routes of administration. The literature contains data on the bioavailability achieved by conventional oral administration and by intravenous administration, from which the relative bioavailability of irinotecan and its active metabolite by conventional oral administration and intravenous administration can be calculated, as shown in Table 16.

TABLE 16

Relative Oral, Non-Gastric Retention Bioavailability of Irinotecan and SN-38 Derived from Literature

|  | m = Irinotecan | m = SN-38 |
|---|---|---|
| $\left[\frac{A^{Oral}_{Total}}{A^{IV}_{Total}}\right]_m$ | 0.12 | 0.16 |
| $\left[\frac{A^{Oral}_{Lactone}}{A^{Oral}_{Total}}\right]_m$ | 0.35 | 0.73 |
| $\left[\frac{A^{IV}_{Lactone}}{A^{IV}_{Total}}\right]_m$ | 0.35 | 0.50 |
| Calculated Relative Bioavailabilty of Lactone $[A^{Oral}_{Lactone}/A^{IV}_{Lactone}]_m$ | 0.12 | 0.22 |

Drengler, R. L. et. al., "Phase I and Pharmacokinetic Trial of Oral Irinotecan Administered Daily for 5 Days Every 3 Weeks in Patients with Solid Tumors", Journal of Clinical Oncology (1999), 17, 685–696.

As can be seen, the relative bioavailability of both the irinotecan and SN-38 lactones when irinotecan is administered orally is less than 25% of their bioavailability when irinotecan is administered intravenously.

It will be seen that gastric delivery of irinotecan greatly increases the bioavailability of the metabolite. By increasing the ratio of SN-38 that is adsorbed in the lactone form $$([A^{GR}_{Lactone}/A^{GR}_{Total}]_{SN-38})$$

from 0.73 to 0.9 and increasing overall delivery of SN-38 to the bloodstream $$([A^{GR}_{lactone}/A^{IV}_{Total}]_{SN-38})$$

from 0.16 to 0.4 through retention of the irinotecan in the absorbing region of the GI tract, one achieves more than half the intravenous bioavailability of SN-38. In fact, one achieves a bioavailability of SN-38 of 0.7 relative to its intravenous bioavailability. Improvement in the absorption of irinotecan and the proportion that is absorbed in lactone form is also achieved (e.g. 0.12→0.2 and 0.35→0.5, respectively). Since SN-38 is a thousand times more potent than irinotecan, an increase in degree of SN-38 absorption and the proportion of SN-38 absorbed in the lactone form are significant results caused by gastric retention.

Such improvement makes gastric oral delivery of irinotecan a viable option compared to i.v. delivery and, actually, an improved option in light of the greater effectiveness of more sustained low dose administration of irinotecan over less frequent high dose treatment. Embodiments of the gastric retention dosage forms of this invention are adapted for sustained, delay and pulsed release (and combinations thereof) Moreover, the ability to administer them orally in a home setting permits increased dosage frequency without inconvenience to the patient or caregiver.

Example 7

Liquid Formulation of Paclitaxel for Gastric Delivery

Introduction

Oral dosing of paclitaxel is limited by paclitaxel's insolubility and by its active exclusion from intestinal absorption by P-glycoprotein pumps that cause drug resistance. Paclitaxel can be formulated in a soluble form by complexing it with human serum albumin (WO 99/13914) obtaining a solution of 1 mg/ml paclitaxel. Oral dosing of this formulation will not lead to a greatly improved bioavailability because the Pgp pumps are still preventing the absorption of the drug. Gastric delivery of the formulation should allow its oral delivery by forcing the drug to be absorbed mostly in the stomach and thus avoiding the areas of maximum Pgp pump activity.

Methods

Three rabbits weighing 2.5 kg each are used in a 3 way crossover study to determine the AUC of bloodstream concentration of paclitaxel versus time after oral administration of a gastric retention liquid formulation of paclitaxel-albumin complex according to the invention and an aqueous solution of a paclitaxel-albumin complex. Blood samples are taken at predetermined intervals and the concentration of paclitaxel is determined by HPLC methods.

Test Solutions

A solution of paclitaxel albumin complex (1 mg/ml paclitaxel) is mixed with an equal volume 2% solution of sodium alginate and an equivalent of encapsulated pellet form of calcium carbonate. The suspension is well mixed and 20 ml containing 10 mg of paclitaxel is administered into the stomach of each rabbit. The alginate will react with the released calcium to form a mixed insoluble calcium alginate—alginic acid gel which traps the albumin-paclitaxel complex. The carbon dioxide gas released makes the mass of the gel float on the stomach contents. The size of the gelatinous mass and its property of floating give the mass gastric retentive properties.

As a negative control, 10 ml of paclitaxel albumin is diluted with 10 ml water and 20 ml is administered into the stomach of a 2.5 kg rabbit.

As a positive control, 1 mg of paclitaxel in the form of the paclitaxel albumin complex is administered intravenously to the rabbit.

Blood Sampling

Blood is drawn from a vein in the rabbit's ear. A blood sample of 0.5 ml is taken from the rabbit prior to dosing and at 0.25, 0.5, 1, 2, 4 and 6 hours in heparanized test tubes. The samples are centrifuged and the plasma frozen at −70° C. for subsequent analysis by HPLC by literature methods.

Results

Paclitaxel concentrations in the plasma are measured by HPLC and plotted against time for all three dosing regimens. The values for the individual rabbits are averaged. The normalized AUCs are calculated for each. The ratio of the AUC for each oral dosing method to that obtained from i.v. dosing is the relative bioavailability of the drug by that method. Paclitaxel administered in an aqeous solution of the paclitaxel albumin complex has low oral bioavailability, e.g. a relative bioavailability of about 5%. The gastric retention liquid formulation has a higher bioavailability, e.g. a relative bioavailability of ~10%, representing a two fold improvement over non-gastric retention oral delivery of the paclitaxel.

Having thus described the invention with reference to certain preferred embodiments, other embodiments will become apparent to one skilled in the art from consideration of the specification and examples. It is intended that the specification, including the examples, is considered exemplary only, with the scope and spirit of the invention being indicated by the claims which follow.

What is claimed is:

1. A method of inhibiting cell proliferation in a tumor of a patient by orally administering a gastric retention solid dosage form or liquid composition containing irinotecan to the patient,
   wherein the dosage form or liquid composition is retained in the stomach for a period of three hours or more and releases the irinotecan in the patient's stomach and at least a portion of the released irinotecan is converted into a metabolite before it is absorbed into the patient's bloodstream,
   wherein the metabolite can exist in an active lactone form and an inactive hydroxy acid form,
   wherein, the bioavailability of the lactone form of the metabolite is greater than the bioavailability of the lactone form of the metabolite when irinotecan is administered in a non-gastric retention solid dosage form or liquid composition, resulting in enhanced systemic delivery of the active form of the metabolite to the tumor.

2. The method of claim 1 wherein bioavailability is measured by the area under a curve of bloodstream concentration of the metabolite versus time.

3. The method of claim 2 wherein the relative bioavailability of the lactone form of the metabolite versus intravenous bioavailability, taken as the area under the bloodstream concentration curve for gastric retention administration divided by the area under the bloodstream concentration curve for intravenous administration, is about 0.5 or higher.

4. A solid pharmaceutical dosage form for enhanced systemic delivery of irinotecan comprising irinotecan and a gastric retention vehicle composition comprising a hydrogel, wherein the dosage form expands upon contact with gastric fluid and wherein after ingestion by a patient the gastric retention vehicle composition expands to retain the dosage form in the patient's stomach for a period of three hours or more.

5. A method of inhibiting cell proliferation in a tumor of a patient afflicted with meta-static carcinoma of the colon or rectum by orally administering a dosage form of claim 4 to the patient.

6. A method of inhibiting cell proliferation in a tumor of a patient afflicted with meta-static carcinoma of the colon or rectum by executing a therapeutic program of repeated oral administration of dosage forms of claim 4 to the patient.

7. The method of claim 6 wherein the dosage forms contain a unit dose of from about 20 to about 250 milligrams of irinotecan.

8. The solid pharmaceutical dosage form of claim 4 wherein the gastric retention vehicle composition further comprises tannic acid.

9. The solid pharmaceutical dosage form of claim 4 wherein the gastric retention vehicle composition further comprises a superdisintegrant.

10. The solid pharmaceutical dosage form of claim 9 wherein the superdisintegrant is selected from the group consisting of crospovidone, croscarmellose sodium, sodium starch glycolate and mixtures thereof.

11. The solid pharmaceutical dosage form of claim 9 wherein the hydrogel is selected from the group consisting of hydroxypropyl methylcellulose and mixtures of hydroxypropyl methylcellulose and hydroxypropylcellulose.

12. The solid pharmaceutical dosage form of claim 11 wherein the gastric retention vehicle composition comprises:
    a) from about 20 to about 70 weight percent of the hydrogel, the hydrogel comprising hydroxypropyl methylcellulose and hydroxypropylcellulose in a weight ratio of from about 1:3 to about 5:3;
    b) from about 25 to about 75 weight percent of the superdisintegrant; and
    c) from about 2 to about 10 weight percent tannic acid.

13. The solid pharmaceutical dosage form of claim 12 wherein the gastric retention vehicle composition comprises:
    a) from about 30 to about 55 weight percent superdisintegrant,
    b) about 5±2 weight percent tannic acid, and
    c) an amount of hydrogel sufficient to bring the total weight percent to 100.

14. The solid pharmaceutical dosage form of claim 12 wherein the gastric retention vehicle composition comprises:
    a) from about 10 to about 20 weight percent hydroxypropyl methylcellulose,
    b) from about 45 to about 50 weight percent hydroxypropyl cellulose,
    c) from about 25 to about 35 weight percent sodium starch glycolate, and
    d) from about 4 to about 10 weight percent tannic acid.

15. The solid pharmaceutical dosage form of claim 12 wherein the gastric retention vehicle composition comprises:

a) from about 10 to about 30 weight percent hydroxypropyl methylcellulose,
b) from about 40 to about 60 weight percent hydroxypropyl cellulose,
c) from about 7 to about 35 weight percent croscarmellose sodium, and
d) from about 4 to about 10 weight percent tannic acid.

16. The solid pharmaceutical dosage form of claim 4 wherein the dosage form is retained in the patient's stomach for about five hours or more.

17. The solid pharmaceutical dosage form of claim 4 wherein the gastric retention vehicle composition expands in volume at least about three fold.

18. The solid pharmaceutical dosage form of claim 17 wherein the gastric retention vehicle composition expands in volume at least about five fold.

19. The solid pharmaceutical dosage form of claim 18 wherein the gastric retention vehicle composition expands in volume at least about eight about fold.

20. The solid pharmaceutical dosage form of claim 4 wherein the gastric retention vehicle composition expands to its fullest extent within about fifteen minutes.

21. The solid pharmaceutical dosage form of claim 20 wherein the gastric retention vehicle composition expands to its fullest extent within about five minutes.

22. The solid pharmaceutical dosage form of claim 4 in the form of a capsule comprising an acid degradable shell and the irinotecan and gastric retention vehicle composition as filling.

23. The solid pharmaceutical dosage form of claim 4 wherein the dosage form is ovoid or elliptical in shape.

24. The solid pharmaceutical dosage form of claim 23 having dimensions of from about 4 mm to about 8 mm in two dimensions and from about 10 mm to about 20 mm in the third dimension.

25. The solid pharmaceutical dosage form of claim 24 having dimensions of about 6 mm by about 6 mm by about 16 mm.

* * * * *